United States Patent [19]

Heslot et al.

[11] 4,172,764

[45] Oct. 30, 1979

[54] PROCESS FOR OBTAINING HYBRID STRAINS OF YEASTS

[75] Inventors: Henri Heslot, Paris; Anne Provost, Massy; Philippe Fournier, Versailles, all of France

[73] Assignee: Agence Nationale de Valorisation de la Recherche (ANVAR), Neuilly sur Seine, France

[21] Appl. No.: 834,937

[22] Filed: Sep. 20, 1977

[30] Foreign Application Priority Data

Sep. 21, 1976 [FR] France ............................... 76 28360

[51] Int. Cl.² ............................................... C12K 1/02
[52] U.S. Cl. .................................. 435/172; 435/924; 435/248; 435/249; 435/259; 435/267
[58] Field of Search ...................... 195/82, 78, 79, 76, 195/1

[56] References Cited

U.S. PATENT DOCUMENTS 3,855,063  12/1974  Nagasawa et al. .................... 195/79

OTHER PUBLICATIONS

Ferenczy et al., Nature, vol. 248, pp. 793 & 794 (1974).
Ferenczy et al., Experientia 31/1, pp. 50-52 (1975).
Ferenczy et al., Experientia 31/9, pp. 1028-1030.
Fodor et al., Proc. Natl. Acad. Sci. U.S.A., vol. 73, No. 6, pp. 2147-2150, Jun. 1976.

*Primary Examiner*—Alvin E. Tanenholtz
*Attorney, Agent, or Firm*—Cullen, Sloman, Cantor, Grauer, Scott & Rutherford

[57] ABSTRACT

The cell walls are removed from two distinct auxotropic mutant strains of yeast. The protoplasts thus obtained are fused and the cell walls regenerated. The strains obtained are cultured on a medium where the original auxotrophs cannot develop and the hybrid or recombinant strains are recovered. The strains obtained by the process are useful for preparing yeast proteins.

13 Claims, No Drawings

PROCESS FOR OBTAINING HYBRID STRAINS OF YEASTS

The present invention relates to a process for obtaining hybrid strains of yeasts, the strains obtained in this way and their use in industry, particularly in the protein-preparation industry.

The micro-organisms used in industrial processes are often devoid of sexuality and it is therefore difficult or impossible to cross-breed strains for obtaining hybrid and/or recombinant forms combining desirable properties.

These difficulties can be overcome when there is a parasexual cycle. This is the case, in particular, with the Penicillium and Aspergillus species. This parasexual cycle presupposes the existence of a heterocaryotic mycelium in which the nuclei of the two parent strains coexist and are able to fuse to give a heterozygotic diploid nucleus which is likely to lead to diploid or haploid recombinants.

In numerous cases of industrial micro-organisms (bacteria, yeast, filamentous fungi) there is no heterocaryotic stage and the above method cannot be applied.

The present invention proposes a process for obtaining hybrid strains of yeasts uniting, in particular, the useful properties of the parent strains.

It relates to a process for obtaining hybrid or recombinant strains of yeasts (H) from two parent strains P1 and P2, characterised in that:
(a) Auxotrophic mutant strains AP 1 and AP 2 of P1 and P2 having distinct auxotrophies are used,
(b) the walls are removed from the cells of the AP 1 and AP 2 strains and the protoplasts thus obtained are fused,
(c) the products of fusion are placed in a medium which promotes the regeneration of the walls,
(d) the strains obtained are cultured on a medium where the AP 1 and AP 2 strains cannot develop owing to their auxotrophic nature,
(e) the H strains which grow in these conditions are stabilised.

In the preferred method of carrying out the process according to the present invention, the walls are removed from the cells of the AP 1 and AP 2 strains by enzymatic treatment and the protoplasts are fused in the presence of polyethylene glycol. The enzyme or enzymes to be used depend upon the strain and the nature of its wall, but may be determined experimentally from the numerous existing enzymatic preparations or may be prepared easily. Thus, the helicase sold by the firm Industrie Biologique Francaise (Gennevilliers) and composed of the digestive juice of Helix Pomatia may be used, in particular, as an enzyme. The enzyme or enzymes will preferably be used in a high pressure osmotic medium containing, for example, a salt such as KCl, $MgSO_4$ and/or a polyol such as mannitol, sorbitol or dithiothreitol.

The walls are preferably digested at a temperature of the order of 30° C. for a period of one or more hours.

Due to their fragility, the protoplasts have to be treated in a hypertonic medium, as mentioned above, until the walls have been regenerated.

The protoplasts are fused in a suitable manner by using polyethylene glycol which tends to form aggregates of protoplasts. A polyethylene glycol of the PEG 400-8000 type and preferably the PEG 6000 type may, for example, be used.

The medium used for promoting the regeneration of the cell walls is a hypertonic culture medium, and preferably a so-called minimal medium, that is to say only containing a source of inorganic nitrogen such as an ammonium salt, a source of organic carbon such as a sugar, trace elements, one or more vitamins and a substance (salt or polyol) giving it a high osmotic force.

After a certain period of regeneration of the order of several hours, the cells obtained may be washed and again spread out on a minimal medium where only the prototrophic strains develop. However, a medium complemented in such a way that certain auxotrophic strains develop without the parent auxotrophic strains being able to develop may also be used for regeneration and selection, as described more fully in example 1.

Strains which are prototrophic or not, which have thus been selected and which are different from the parent auxotrophic strains are heterocaryons which contain a nucleus of each parent. These strains tend to segregate the two parental types, but prolonged culture allows them to be stabilised. They are therefore uninucleated.

The auxotrophic strains used may either be natural or be obtained from corresponding prototrophic strains by mutation and selection.

The processes of mutation and selection for the auxotrophic strains are known to the skilled man. Thus a strain which is to be mutated may be placed in the presence of a physical or chemical mutagen, for example X-rays, γ-rays and ultra-violet rays or ethylmethanesulfonate, nitrous acid, alkylating agents, nitrosoguanidine, etc.

Selection is then carried out by culturing the strains which have been subjected to the mutagen treatment in a minimal medium where only the prototrophic strains are able to develop. The useful strains can therefore be recognised as the strains which do not proliferate on this medium. However, in view of the difficulty of this direct selection, treatment is usually carried out using an antifungal agent which kills the growing cells selectively. In this way, the auxotrophic strains are concentrated.

It is thus possible to obtain strains marked with certain auxotrophies and, if desired, these strains may be subjected to another mutagen treatment in order to obtain double-auxotrophic strains.

The process according to the present invention is particularly useful for cross-breeding strains of yeasts each having valuable industrial properties which are worth combining in a single strain.

Therefore, when preparing proteins by culturing yeasts on an amylaceous medium, two strains of yeasts, an amylolytic strain and a strain using sugars are at present employed; with the process of the present invention, an amylolytic strain may be obtained which also employs sugars. Suitable amylolytic yeast strains include, preferably, *Endomycopsis*, for example: *Endomycopsis (Candida) Chodati* or *Endomycopsis Fibuligera* and suitable strains using sugars include strains belonging to the species *Candida, saccharomycopsis, Torulopsis, Torula, Saccharomyces, Hansenula, Kluyveromyces*, for example *Candida Tropicalis, Candida guillermondii, Saccharomycopsis (Candida) lipolytica, Candida (Torulopsis) utilis, Saccharomyces cerevisiae, Kluyveromyces (Saccharomyces), fragilis, Hansenula anomala, Hansenula saturnus (H. Suaveoleus), Hansenula jadinii* and *Rhodotorula rubra (R. mucilaginosa)*. A hybrid or a recombinant obtained from a strain of each of the above groups may allow the production of proteins on an amylaceous medium to be improved, particularly if the strain using sugars has a high protein content.

The present invention also allows polyploid strains which are much larger than the parent strains to be prepared. This is useful when separating the strains from the culture medium. When the parent strains are strains (such as *Candida tropicalis*) growing on hydrocarbon products, it is particularly useful to be able to separate them easily from the culture medium which cannot be assimilated in food.

The present invention also relates to strains obtained by the process according to the present invention as well as the applications of the said strains, in particular those enumerated above, in the preparation of alimentary proteins on a culture medium which is both amylaceous and hydrocarbonic.

The following Examples are intended to illustrate the present invention without limiting the scope thereof.

EXAMPLE 1

Obtaining hybrid strains from two strains of the petroleum yeast *Candida tropicalis*

Up until now it has not been possible to cross-breed strains of this species, owing to the absence of a well-defined sexual cycle.

The process of the present invention has allowed stable hybrids of *C. tropicalis* to be obtained for the first time.

The starting strains of *C. tropicalis* which are to be cross-bred are capable of growing in a minimal medium designated hereafter by MM. This medium contains 2% of glucose, 0.5% of ammonium sulphate, mineral salts and two vitamins, biotin and thiamin (cf. Leupold, Switzerland. Z. all. Path. Bakt. 1955, 15, 1141–1146).

Each strain is treated separately by $\gamma$ irradiation (75 Krad) so as to induce auxotrophic mutants having an additional need for an essential metabolite (amino—acid, purine or pyrimidine base, vitamin, etc.).

The auxotrophic mutants are isolated by cultivating the strains obtained on a minimal medium in the presence of nystatin, an antifungal antibiotic which kills the dividing cells preferentially.

By repeating the mutagen treatment on the isolated strains, two double-auxotrophic mutants have been obtained:

AP 1. *C. tropicalis* met⁻his⁻ (methionine and histidine requirement)

AP 2. *C. tropicalis* cyt⁻ade⁻ (cytosine and adenine requirement).

The two strains are cultivated on the YPGT medium described by Svihla et al. (J. Bacteriology, 1961, 82, 808–814) composed of:

| | |
|---|---|
| 0.5 g | yeast extract |
| 0.5 g | Peptone |
| 3 g | glucose |
| 74.5 mg | L-methionine |
| 67.5 mg | DL-homocysteine thiolactone |
| 100 mg | DL-methionine methyl sulfonium chloride |
| 100 ml | distilled water. |

The cells of each parent strain are suspended in this medium and stirred for 4 to 5 hours at 30° C. to ensure that division begins. These cultures are then left overnight at ambient temperature without stirring so as to collect exponential phase cells the following morning. It is necessary to collect about $5.10^8$ cells per strain.

Two washing treatments are carried out with centrifugation and the sediment is suspended in 10 ml of PTP buffer having the following composition:

| | |
|---|---|
| 99 mM | Tris |
| 860 μM | EDTA |
| 50 mM | dithiothreitol. |

This buffer is sterilized by filtration just before use. The cellular suspension is then treated $3 \times 30$ sec. in a low—power MSE sonicator in order to dissociate the clumps of cells, and is then incubated at 30° C. without stirring in such a way that the total treatment time in the PTP does not exceed 10 minutes.

The cells are washed with a solution of KCl at 0.2 M and are again suspended in 4 ml of the following enzymatic solution:

| | |
|---|---|
| 1 ml | digestive juice of *Helix pomatia* (Industrie Biologique Francaise, Gennevilliers) |
| 2 ml | KCl 1.2 M |
| 1 ml | dithiothreitol at 20 mM. |

After 1 hour of incubation without stirring at 30° C., conversion into protoplasts is complete. These protoplasts are then washed with a solution of KCl at 1.2 M+CaCl$_2$ at 0.2%.

In order to fuse the cells, protoplasts from the two parents are mixed in equal quantities. 0.1 ml of the protoplasts suspension; 0.1 ml of polyethylene glycol (PM=6000) at 20%+CaCl$_2$ at 0.2% are placed in an empty sterile Petri dish. The mixture is stirred gently with the end of a sterile glass rod. The mixture is left to act for 6 minutes and the cellular walls are then regenerated by carefully adding (so as not to destroy the clumps of protoplasts formed by the PEG) some liquid minimal medium plus 8% of mannitol. 1.5 ml of this medium are initially introduced into the dish, then 5 minutes later 1 ml, finally 5 minutes later another 1.5 ml. Regeneration is left to take place for at least 4 hours. The cells are then centrifuged, washed and spread out on minimal medium.

The cells of the two parent strains cannot develop on such a medium. However, the appearance of colonies (prototrophic) is observed on the comparison dishes. Caryologic and genetic analysis proves that these are heterocaryotic cells containing a nucleus from each parent. Growth takes place as a result of complementation.

The prototrophs are initially unstable and produce auxotrophic cells of the two parental types. However, stable prototrophs which are no longer segregated in normal conditions can be obtained by prolonged culture on minimal medium and selection. The stabilized strains are composed of uninucleated cells. It should be noted that these cells are not generally (see example 2) larger than cells of the starting strains.

These cells combine genetic markers from the two parent strains in one nucleus and therefore have a hybrid nature.

In order to prove this fact, the stable prototroph may be irradiated with a weak dose of $\gamma$ rays (5 Kr). Auxotrophs having a low frequency (0.5%) appear, but they may be concentrated by nystatin treatment. Analysis of their nutritional requirements reveals the presence of the following types:

| his⁻ | met⁻his⁻ | ade⁻met⁻ |
| met⁻ | cyt⁻ade⁻ | ade⁻his⁻ |
| ade⁻ |  | cyt⁻his⁻ |
| cyt⁻ |  |  |

The parental associations of the markers (met⁻his⁻ and cyt⁻ade⁻) are again found but also the recombinant types which represent various reassociations of the characters contributed by the two parents.

Generally speaking, if the fusion ab×cd of the double-auxotrophic parent strains ab and cd is considered, there are several ways of selecting the products of fusion. In fact, as described above, the cells may be cultured on MM after PEG treatment. It is also possible to use the following media where the selection only relates to two markers:

| MM + a + c | MM + b + c |
| MM + a + d | MM + b + d | or to three markers:

| MM + c | MM + a |
| MM + d | MM + b | which allows certain types of recombinants to be selected.

With regard to industrial applications, the important properties will frequently have polygenetic determinism (heat-resistance, protein content, growth-rate ...). The method described above may however be applied to them. It is now necessary to examine which of the recombinants have new and desirable industrial properties.

By way of example, it may be assumed that one strain flocculates well, thus making it much easier to separate the cells from the culture medium by decantation or centrifugation. It will also be assumed that this strain has a low protein content and an average growth rate.

If another non-flocculant but rapidly dividing and protein-rich strain is available, it will be useful to cross-breed it with the first strain. New strains combining the useful properties of the two parents (good flocculation, rapid growth, high protein content) will thus be selected from the recombinants.

EXAMPLE 2

Obtaining a polyploid strain from two strains of the petroleum yeast *Candida tropicalis*

The starting strains to be cross-bred are two auxotrophic strains:

*C. tropicalis* leu⁻ (leucine requirement)
*C. tropicalis* cyt⁻ (cytosine requirement).

They are fused by the method described in Example 1.

The colonies which are composed of larger cells than those of the parent strain are sought by microscopic examination of the colonies which develop on minimal medium. An exact case is provided by the prototroph P-1, the properties of which are as follows: (in arbitrary units)

average diameter of cells of the parent leu⁻: 7.9
average diameter of cells of the parent cyt⁻: 6.8
average diameter of cells of the prototrophe P-1: 10.3.

It is obvious that the volume of the cells of this prototroph is approximately double that of the average of the cell volumes of the parent strains. This is very certainly a polyploid form (4n if the initial strains are 2n).

Polyploid strains of this type are of industrial interest because their larger cells make separation easier (thus less costly in power) by decantation or centrifugation from the culture medium. In addition, their nutritional value is improved, owing to the reduction of the percentage of walls, an element which is usually hardly digestible.

The strains thus obtained are more particularly useful in the preparation of proteins from petroleum by-products.

EXAMPLE 3

Obtaining hybrid strains between the petroleum yeast *Candida tropicalis* and the amylolytic yeast *Endomycopsis fibuligera*

The strain of *C. Tropicalis* used is the double auxotrophic mutant cyt⁻ade⁻ of Example 1.

In contrast, all of the *Endomycopsis fibuligera* strains, in addition to their biotin and thiamin requirements, also require a supply of pyridoxine and methionine. They are incapable of growing on the minimal medium described in Example 1. The natural auxotrophies are therefore sufficient for hybridization.

The method carried out for preparing the protoplasts of *E. fibuligera* does not differ from that described for *C. tropicalis*.

The methods for fusing and regenerating the walls are identical to those in Example 1. After PEG treatment, the cells are cultured on minimal medium. Prototrophic colonies develop.

Thirteen of these prototrophs have been isolated and examined. They have been designated II-1 ... II-13.

Table 1 gives the comparative properties of these strains and of the two parent strains.

The capacities of assimilating a certain number of carbon substrates have been shown; the cellular morphology, the intra- and extra-cellular amylolytic activities, the methionine requirement, the adenine and cytosine requirements.

It is obvious that the H-1 ... H-13 strains have a reassociation of the parental properties and consequently have the structure of hybrids.

Table 2 gives the dry weights obtained and the protein contents after 72 hours of culture on soluble starch minimal medium. The strains used in these tests have been subjected to preliminary culture on glucose.

Finally, Table 3 shows the results obtained when the strains have been subjected to preliminary culture on soluble starch. It will be noted that the dry weights are much higher in this case.

The H-1 hybrid was subjected to continuous culture at 30° C. in the mineral medium having a base supplemented with 3% of ground corn and 0.5% of corn-steep. After 200 hours of culture, and for a rate of dilution d=0.125, a dry weight of 20.9 g/liter was obtained with a protein content of 22.5%, thus a total of 4.7 g/liter of proteins.

TABLE 1

PROPERTIES OF THE PARENT SPECIES AND THE DERIVATIVE HYBRID STRAINS

| Assimilated Compounds | EF | C.T. | H1 | H2 | H3 | H4 | H5 | H6 | H7 | H8 | H9 | H10 | H11 | H12 | H13 |
|---|---|---|---|---|---|---|---|---|---|---|---|---|---|---|---|
| Sorbox | o | + | + | o | o | o | o | + | o | + | o | o | o | o | o | ± |
| Erythritol | + | o | o | ± | + | o | o | o | o | o | o | o | + | + | o | o |
| Trehalose | o | + | + | + | + | o | ± | + | + | + | + | + | + | o | + | + |
| Xylose | o | + | + | o | o | o | o | o | + | o | + | + | + | ± | + | ± |
| Inositol | + | o | o | + | + | + | + | + | + | + | + | + | + | + | o | + |
| Mannitol | o | + | + | + | + | + | o | + | o | + | o | o | + | + | + | + |
| n-paraffins (C16) | o | + | + | + | + | + | + | + | + | + | + | + | + | + | + | + |
| Cellular morphology | F | CI | CI | F | F | F | F | F | F | CI | CI | CI | F | F | CI | CI |
| intracellular enzymatic activities | BAM + AMGL | BAM | BAM + AMGL | BAM + AMGL | BAM | BAM + AMGL | BAM + weak AMGL | BAM | BAM + AMGL | BAM + AMGL | BAM + AMGL | BAM + AMGL | BAM + AMGL | BAM + AMGL | BAM + AMGL | BAM + weak AMGL |
| AMGL activity in the culture medium | + | o | o | o | o | + | o | o | o | o | + | + | + | + | + | + |
| methionine requirement | + | o | o | o | + | + | + | + | + | o | o | o | + | o | o | o |
| pyridoxine requirement | + | o | o | o | o | o | o | o | o | o | o | o | o | o | o | o |
| adenine + cytosine requirement | o | + | o | o | o | o | o | o | o | o | o | o | o | o | o | o |

Abbreviations
EF = Endomycopsis filubigera
CT = Candida tropicalis
H1 .... H13 = hybrid strains
F = Filaments
CI = Isolated cells
BAM = βamylase
AMGL = amyloglucosidase

TABLE 2
DRY WEIGHT AND PROTEIN CONTENT AFTER 72 HOURS OF CULTURE ON SOLUBLE STARCH MINIMAL MEDIUM

|  | E.F. | C.T. | $H_1$ | $H_2$ | $H_3$ | $H_4$ | $H_5$ | $H_6$ | $H_7$ | $H_8$ | $H_9$ | $H_{10}$ | $H_{11}$ | $H_{12}$ | $H_{13}$ |
|---|---|---|---|---|---|---|---|---|---|---|---|---|---|---|---|
| Dry weight (g/liter) | 3.48 | 5.56 | 5.56 | 3.89 | 3.83 | 3.95 | 6.23 | 2.2 | 5.49 | 5.05 | 5.36 | 5.54 | 4.41 | 5.71 | 5.52 |
| Percentage Protein Content | 27.10 | 32.10 | 34.60 | 23.40 | 31.20 | 28.20 | 29.80 | 29.60 | 32.80 | 33.80 | 34.00 | 33.20 | 32.70 | 30.00 | 41.30 |
| Proteins in g/l | 0.93 | 1.35 | 1.93 | 0.91 | 1.19 | 1.11 | 1.86 | 0.65 | 1.8 | 1.71 | 1.83 | 1.84 | 1.44 | 1.71 | 2.28 |
| Residual starch /(mg/l) | 180 | 860 | 960 | 320 | 90 | 40 | 130 | 20 | 600 | 500 | 970 | 150 | 80 | 600 | 20 |
| Residual Glucos (mg/l) | 36 | 36 | 23.6 | 12 | 16 | 16 | 266 | 20 | 220 | 272 | 330 | 32 | 28 | 334 | 700 |

Abbreviations
E.F. = Endomycopsis filubigera
C.T. = Candida Tropicalis
$H_1 \ldots H_{13}$ = hybrid strains
Culture medium: minimal medium for 1 liter of medium
15 g of $SO_4(NH_4)_2$, 4.5 kg of $KH_2PO_4$, 20 g of soluble starch; 50 ml of distilled water is then poured and the pH is brought to 4.5.
0.85 g of $MgCl_2(OH_2)_6$, 0.5 g of NaCl, 0.05g of $CaCl_2$ and 0.005g of $FeCl_3$ and 4 growth factors are then added.
5 mg of Thiamine, 60 μg of biotin, 100 mg of methionine, 3 mg of pyridoxine 11 ml of buffer are then added: 3.75 ml of lactic acid for 40 ml of sodium lactate made up to 1 l with distilled water

TABLE 3
DRY WEIGHT AND PROTEIN CONTENT AFTER 72 HOURS OF CULTURE ON SOLUBLE STARCH MINIMAL MEDIUM, CULTURE HAVING STARTED WITH THE CULTURES FROM TABLE 2

|  | $H_1$ | $H_{10}$ | $H_{13}$ |
|---|---|---|---|
| Dry weight (g/liter) | 11,8 | 13,4 | 12,3 |
| Protein Content (%) | 35,0 | 33,3 | 38,13 |
| Proteins (in g/liter) | 4,13 | 4,45 | 4,7 |
| Residual starch (mg/liter) | 0 | 0 | 0 |
| Residual glucose (mg/liter) | 184 | 68 | 620 |

Abbreviations
$H_1 \ldots H_{13}$ : hybrid strains
The culture medium is the same as in Table 2.

We claim:

1. A process for obtaining strains of hybrid or recombinant (H) yeasts from two parent strains P1 and P2, comprising the following steps:
   (a) removing the walls from the cells of auxotrophic mutant strains AP 1 and AP 2 having distinct auxotrophies and derived from said two parent strains,
   (b) fusing the protoplasts thus obtained,
   (c) placing the products of fusion in a medium promoting the regeneration of the walls,
   (d) culturing the strains obtained on a medium where said auxotrophic mutant strains cannot develop owing to their auxotrophic nature, and
   (e) stabilizing said strains of hybrid or recombinant yeasts which grow in these conditions and therefore producing a uninucleated hybrid or recombinant strain having the genetic information of the corresponding parent strains.

2. A process according to claim 1, in which the walls are removed from the cells of said auxotrophic mutant strains by enzymatic treatment and fusion is carried out in the presence of polyethylene glycol.

3. A process according to claim 1 in which steps a, b and c of the process are carried out in a hypertonic medium.

4. A process according to claim 1 in which the medium which promotes the regeneration of the walls is a hypertonic minimal medium containing a source of inorganic nitrogen, a source of organic carbon, trace elements, one or more vitamins, and a substance giving it a high osmotic pressure.

5. A process according to claim 1 in which the strains obtained in step c are cultured on a minimal medium containing a source of mineral nitrogen, a source of organic carbon, trace elements and one or more vitamins.

6. A process according to claim 1 in which said auxotrophic mutant strains are obtained from said two parent strains by mutation and selection.

7. A process according to claim 1 in which the hybrid or recombinant strains obtained are polyploids which are larger than those of said auxotrophic mutant strains.

8. A process according to claim 7, in which said auxotrophic mutant strains are *Candida tropicalis* strains each having a single auxotrophy.

9. A process according to claim 1 in which one of said parent strains is selected from yeasts having amylolytic activity and said other parent strain is selected from yeasts growing on sugars and/or n-paraffins.

10. A process for obtaining yeast proteins, which comprises culturing a hybrid or recombinant strain produced by the process of claim 1, and recovering protein from the culture.

11. A process for obtaining yeast proteins which comprises culturing the hybrid or recombinant strain produced by the process of claim 7 and recovering the protein from the culture.

12. A process according to claim 11, in which the strain used is a polyploid grown on petroleum by-products.

13. A process according to claim 11, in which the strain used is a hybrid or recombinant of amylolytic yeast and of yeast grown on sugars and/or n-paraffins.